United States Patent
Sheng

(10) Patent No.: US 11,691,030 B2
(45) Date of Patent: Jul. 4, 2023

(54) SYSTEM AND METHOD FOR OPTIMIZED DYNAMIC COLLIMATOR ROTATION IN VOLUMETRIC MODULATED ARC THERAPY

(71) Applicant: The Regents of the University of California, Oakland, CA (US)

(72) Inventor: Ke Sheng, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 508 days.

(21) Appl. No.: 16/606,039

(22) PCT Filed: Apr. 18, 2018

(86) PCT No.: PCT/US2018/028086
§ 371 (c)(1),
(2) Date: Oct. 17, 2019

(87) PCT Pub. No.: WO2018/195151
PCT Pub. Date: Oct. 25, 2018

(65) Prior Publication Data
US 2020/0139156 A1    May 7, 2020

Related U.S. Application Data

(60) Provisional application No. 62/486,727, filed on Apr. 18, 2017.

(51) Int. Cl.
*A61N 5/10*    (2006.01)
*G16H 30/20*   (2018.01)

(52) U.S. Cl.
CPC ......... *A61N 5/1047* (2013.01); *A61N 5/1037* (2013.01); *A61N 5/1039* (2013.01);
(Continued)

(58) Field of Classification Search
CPC .. A61N 5/1031; A61N 5/1042; A61N 5/1047; A61N 5/103; A61N 5/1036; A61N 5/1037; A61N 5/1039; A61N 5/1067
See application file for complete search history.

(56) References Cited

U.S. PATENT DOCUMENTS 9,764,162 B1 *  9/2017  Willcut ................ G06T 7/0014
2013/0131428 A1  5/2013  Jiang
(Continued)

FOREIGN PATENT DOCUMENTS

WO    2016081916 A1    5/2016
WO    2017156316 A1    9/2017

OTHER PUBLICATIONS

Bedford J. L., "Treatment planning for volumetric modulated arc therapy," Med. Phys. 36, 5128-5138 (2009).10.1118/1.3240488.
(Continued)

*Primary Examiner* — Christine H Matthews
(74) *Attorney, Agent, or Firm* — Quarles & Brady LLP

(57) ABSTRACT

Systems and method for generating and executing volumetric modulated arc therapy ("VMAT") plans are provided. In some aspects, the method includes receiving a representation of a subject comprising information related to target and non-target volumes of interest, and generating an objective function based on the representation of the subject, wherein the objective function accounts for dynamic collimator rotation. The method also includes performing an iterative optimization process, using the objective function, to generate a dynamic collimator VMAT plan, and generating a report in accordance with the dynamic collimator VMAT plan.

20 Claims, 6 Drawing Sheets

(52) U.S. Cl.
CPC ........... *A61N 5/1067* (2013.01); *G16H 30/20* (2018.01); *A61N 5/1036* (2013.01)

(56) References Cited

U.S. PATENT DOCUMENTS

2018/0243584 A1* 8/2018 Nord ................ A61N 5/1048
2019/0099620 A1* 4/2019 Isola ................ A61N 5/1037

OTHER PUBLICATIONS

Bortfeld T. et al., "Single-arc IMRT?," Phys. Med. Biol. 54, N9-N20 (2009).10.1088/0031-9155/54/1/N02.
Bratengeier K., "2-Step IMAT and 2-Step IMRT in three dimensions," Med. Phys. 32, 3849-3861 (2005).10.1118/1.2134928.
Cao D., et al., "A generalized inverse planning tool for volumetric-modulated arc therapy," Phys. Med. Biol. 54, 6725-6738 (2009). 10.1088/0031-9155/54/21/018.
Chambolle A. et al., "A first-order primal-dual algorithm for convex problems with applications to imaging," J. Math. Imaging Vision 40, 120-145 (2011).10.1007/s10851-010-0251-1.
Cheng L.-T., et al., "Binary level-set shape optimization model and algorithm for volumetric modulated arc therapy in radiotherapy treatment," SIAM J. Sci. Comput. 35, B1321-B1340 (2013).10. 1137/120890430.
Condat L., "A primal-dual splitting method for convex optimization involving Lipschitzian, proximable and linear composite terms," J. Optim. Theory Appl. 158, 460-479 (2013).10.1007/s10957-012-0245-9.
Craft D., et al., "Multicriteria VMAT optimization," Med. Phys. 39, 686-696 (2012).10.1118/1.3675601.
Crooks S. M., et al., "Aperture modulated arc therapy," Phys. Med. Biol. 48, 1333-1344 (2003).10.1088/0031-9155/48/10/307.
Dong P., et al., "4pi noncoplanar stereotactic body radiation therapy for centrally located or larger lung tumors," Int. J. Radiat. Oncol., Biol., Phys. 86, 407-413 (2013).10.1016/j.ijrobp.2013.02.002.
Earl M., et al., "Inverse planning for intensity-modulated arc therapy using direct aperture optimization," Phys. Med. Biol. 48, 1075-1089 (2003).10.1088/0031-9155/48/8/309.
Gorski J., et al., "Biconvex sets and optimization with biconvex functions: A survey and extensions," Math. Methods Oper. Res. 66, 373-407 (2007).10.1007/s00186-007-0161-1.
Grégoire V. et al., "State of the art on dose prescription, reporting and recording in Intensity-Modulated Radiation Therapy (ICRU report No. 83)," Cancer/Radiothér. 15, 555-559 (2011).10.1016/j.canrad.2011.04.003.
International Searching Authority, International Search Report and Written Opinion for application PCT/US2018/028086, dated Aug. 28, 2018, 16 pages.
Jin J.-Y., et al., "Advances in treatment techniques: Arc-based and other intensity modulated therapies," Cancer J. 17, 166-176 (2011). 10.1097/PPO.0b013e31821f8318.
Kawashima M., et al., "Comparison of total MU and segment areas in VMAT and step-and-shoot IMRT plans," Radiol. Phys. Technol. 6, 14-20 (2013).10.1007/s12194-012-0164-3.
Kim H., et al., "Dose optimization with first-order total-variation minimization for dense angularly sampled and sparse intensity modulated radiation therapy (DASSIM-RT)," Med. Phys. 39, 4316-4327 (2012).10.1118/1.4729717.
Luan S., et al., "A new MLC segmentation algorithm/software for step-and-shoot IMRT delivery," Med. Phys. 31, 695-707 (2004).10. 1118/1.1646471.
Men C., et al., "An exact approach to direct aperture optimization in IMRT treatment planning," Phys. Med. Biol. 52, 7333-7352 (2007).10.1088/0031-9155/52/24/009.
Neylon J., et al., "A nonvoxel-based dose convolution/superposition algorithm optimized for scalable GPU architectures," Med. Phys. 41, 101711 (15pp.) (2014).10.1118/1.4895822.
Nguyen D., et al., "A novel software and conceptual design of the hardware platform for intensity modulated radiation therapy," Med. Phys. 43, 917-929 (2016).10.1118/14940353.
Nguyen D., et al., "Dose domain regularization of MLC leaf patterns for highly complex IMRT plans," Med. Phys. 42, 1858-1870 (2015).10.1118/1.4915286.
Nguyen, D., et al. "A comprehensive formulation for volumetric modulated arc therapy planning." Medical physics 43.7 (2016): 4263-4272.
Otto K., "Volumetric modulated arc therapy: IMRT in a single gantry arc," Med. Phys. 35, 310-317 (2008).10.1118/1.2818738.
Peng F., et al., "A new column-generation-based algorithm for VMAT treatment plan optimization," Phys. Med. Biol. 57, 4569-4588 (2012).10.1088/0031-9155/57/14/4569.
Que W., "Comparison of algorithms for multileaf collimator field segmentation," Med. Phys. 26, 2390-2396 (1999).10.1118/1. 598755.
Rao M., et al., "Comparison of Elekta VMAT with helical tomotherapy and fixed field IMRT: Plan quality, delivery efficiency and accuracy," Med. Phys. 37, 1350-1359 (2010).10.1118/1.3326965.
Salari E. et al., "A column-generation-based method for multi-criteria direct aperture optimization," Phys. Med. Biol. 58, 621-639 (2013).10.1088/0031-9155/58/3/621.
Shepard D. M., et al., "An arc-sequencing algorithm for intensity modulated arc therapy," Med. Phys. 34, 464-470 (2007).10.1118/ 1.2409239.
Verbakel W. F. A. R., et al., "Volumetric intensity-modulated arc therapy vs conventional IMRT in head-and-neck cancer: A comparative planning and dosimetric study," Int. J. Radiat. Oncol., Biol., Phys. 74, 252-259 (2009).10.1016/i.ijrobp.2008.12.033.
Xia P., et al., "A leaf sequencing algorithm to enlarge treatment field length in IMRT," Med. Phys. 29, 991-998 (2002).10.1118/1. 1477236.
Yu C. X., "Intensity-modulated arc therapy with dynamic multileaf collimation: An alternative to tomotherapy," Phys. Med. Biol. 40, 1435-1449 (1995).10.1088/0031-9155/40/9/004.
Zhu L., et al., "Using total-variation regularization for intensity modulated radiation therapy inverse planning with field-specific numbers of segments," Phys. Med. Biol. 53, 6653-6672 (2008).10. 1088/0031-9155/53/23/002.

* cited by examiner

SYSTEM AND METHOD FOR OPTIMIZED DYNAMIC COLLIMATOR ROTATION IN VOLUMETRIC MODULATED ARC THERAPY

CROSS-REFERENCE TO RELATED APPLICATIONS

This application represents the national stage entry of International Application PCT/US2018/028086, filed on Apr. 18, 2018, which claims benefit of and priority to U.S. Provisional Application No. 62/486,727, filed Apr. 18, 2017, and entitled "SYSTEM AND METHOD FOR OPTIMIZED DYNAMIC COLLIMATOR ROTATION IN VOLUMETRIC MODULATED ARC THERAPY", which is incorporated herein by reference in its entirety for all purposes.

STATEMENT REGARDING FEDERALLY SPONSORED RESEARCH

This invention was made with government support under R43CA183390 and R01CA1883300 awarded by the National Institutes of Health. The government has certain rights in the invention.

BACKGROUND

The present disclosure generally relates to systems and methods for radiation therapy. More particularly, the present disclosure generally relates to systems and methods for designing a radiation treatment plan for a radiation therapy system, such as volumetric modulated arc therapy ("VMAT") system.

Volumetric modulated arc therapy ("VMAT") is becoming a widely adopted radiation treatment technique due to its ability to achieve highly conformal dose distributions when treating subjects using radiation. The theoretical framework of VMAT is based on an earlier technique known as intensity modulated arc therapy ("IMAT"). In IMAT, radiation dose is delivered inside a targeted volume by directing radiation from a number of angles along a given arc, and using various aperture configurations at each beam angle along the arc. However, to achieve satisfactory dose distributions in a targeted volume using IMAT, multiple arcs were often required. Therefore, more practical algorithms, such as VMAT algorithms, employing one or two arcs were subsequently developed.

Compared to the more traditional static beam intensity modulated radiation therapy ("IMRT"), VMAT is significantly more efficient in both treatment time and total monitor units ("MU") for similar dose distributions. However, unlike IMRT, the arc optimization problem presented by VMAT is significantly more complex, due to the substantially increased number beam orientations and mechanical constraints of the gantry and collimator of the treatment machines.

Modern machines utilize rotatable multileaf collimator ("MLC") to shape highly modulated radiation beams. An example MLC having seven rows of paired leaves is illustrated in FIG. 1. The leaves are typically constructed from a high atomic number material, e.g. tungsten, and have a thickness sufficient to block an outgoing beam of radiation. To achieve a desired spatial dose distribution, the position of each individual leaf can be independently controlled to create different windows or apertures shaping the delivered radiation beam. By changing exposure time, leaf positioning and MLC rotation, along with beam angle or beam aim relative to a subject, a customizable dose distribution can be constructed.

Typical MLC leaves are about 5 mm wide, which can be very coarse for tumors with continuous boundaries. To increase resolution, MLCs can be modified to use narrower leaves. However, narrow leaves are more difficult to manufacture, and reduce the field of view due to their mechanical limitations. For example, a high resolution MLC (e.g. with 2.5 mm leaf width) would limit field of view size to 20 cm, compared to the 40 cm field of view size available on standard MLCs. Alternatively, resolution may be increased by replacing the MLC. However, there is no easy way of exchanging MLCs on a single machine. As a result, treatment machines usually have a fixed resolution and field of view size. As such, for smaller clinics, selecting a machine often involves a compromise between resolution and field of view size, which can limit flexibility of treatment. Some larger clinics may have the option of purchasing several machines, each with a different MLC resolution. However, notwithstanding the added cost, subjects cannot be transferred between machines, for example during down time, which affects clinical flow and robustness.

Due to the importance that VMAT plays in today's radiotherapy practice, there is a strong need to overcome the limitations of these existing technologies.

SUMMARY

The present disclosure overcomes the drawbacks of previous technologies by providing a system and method for generating radiotherapy treatment plans for volumetric modulated arc therapy ("VMAT"). In particular, a novel optimization framework is described that incorporates dynamic collimator rotation to achieve optimized VMAT radiotherapy treatment plans.

In accordance with one aspect of the present disclosure, a method for generating a dynamic collimator volumetric modulated arc therapy ("VMAT") plan is provided. The method includes receiving a representation of a subject comprising information related to target and non-target volumes of interest, and generating an objective function based on the representation of the subject, wherein the objective function accounts for dynamic collimator rotation. The method also includes performing an iterative optimization process, using the objective function, to generate a dynamic collimator VMAT plan, and generating a report in accordance with the dynamic collimator VMAT plan.

In accordance with another aspect of the present disclosure, a volumetric modulated arc therapy ("VMAT") system is provided. The system includes a radiation source configured to generate and direct radiation to a subject, and a gantry housing the radiation source and configured to rotate about an axis of rotation. The system also includes a control mechanism configured to control the rotation of the gantry and the delivery of radiation from the radiation source to a target volume in the subject. The system further includes a computer in communication with the control mechanism that is configured to receive a representation of a subject comprising information related to target and non-target volumes of interest. The computer is also configured generate an objective function based on the representation of the subject, wherein the objective function accounts for dynamic collimator rotation, and perform an iterative optimization process using the objective function to generate a dynamic collimator VMAT plan. The computer is further configured to generate and provide control signals to the control mechanism, in accordance with the dynamic collimator VMAT plan, to irradiate the subject.

In accordance with yet another aspect of the present disclosure, a system for generating a dynamic collimator volumetric modulated arc therapy ("VMAT") plan is provided. The system includes an input configured to receive a representation of a subject comprising information related to target and non-target volumes of interest. The system also includes an optimizer engine, in communication with the input, having at least one processor programmed to receive the representation of the subject, and apply an optimization framework to generate a dynamic collimator VMAT plan. The at least one processor is also configured to generate a report in accordance with the dynamic collimator VMAT plan. The system further includes an output for providing the report.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Volumetric modulated arc therapy ("VMAT") is a widely-employed radiation therapy technique that can achieve dosimetry comparable with static beam intensity modulated radiation therapy ("IMRT") while reducing monitor units and treatment time. However, common VMAT optimization techniques often utilize greedy heuristics that produce empirical solutions, which can jeopardize plan consistency and quality. In addition, given the complexity of VMAT, these techniques typically implement algorithms based on static, non-rotated collimator arrangements, which limits the achievable resolution.

To overcome the drawbacks of these previous methods, the present disclosure provides a novel optimization framework, referred to as dynamic collimator VMAT. This approach utilizes dynamic collimator rotation to generate optimized VMAT radiotherapy plans. As appreciated from descriptions below, the present system and method can be used to increase the achievable collimator resolution for a given radiation machine without need for costly collimator replacement or upgrades.

Figure 1:
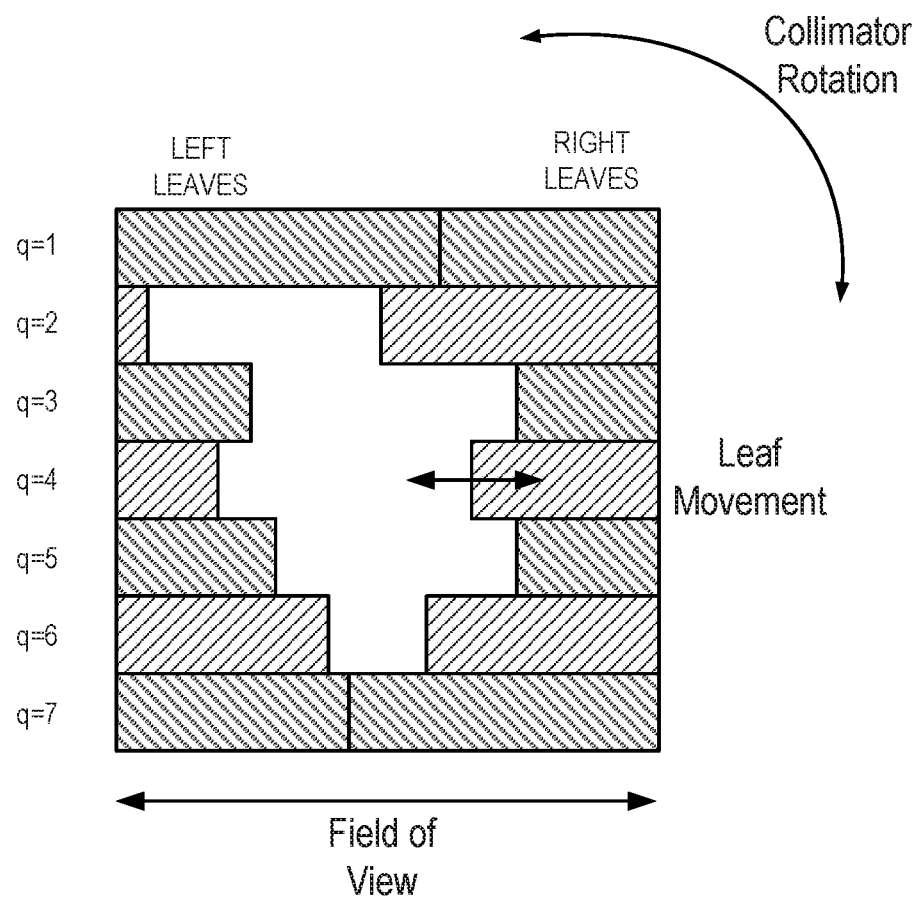
FIG. 1 is a graphic illustration of an example multileaf collimator ("MLC")
Figure 2:
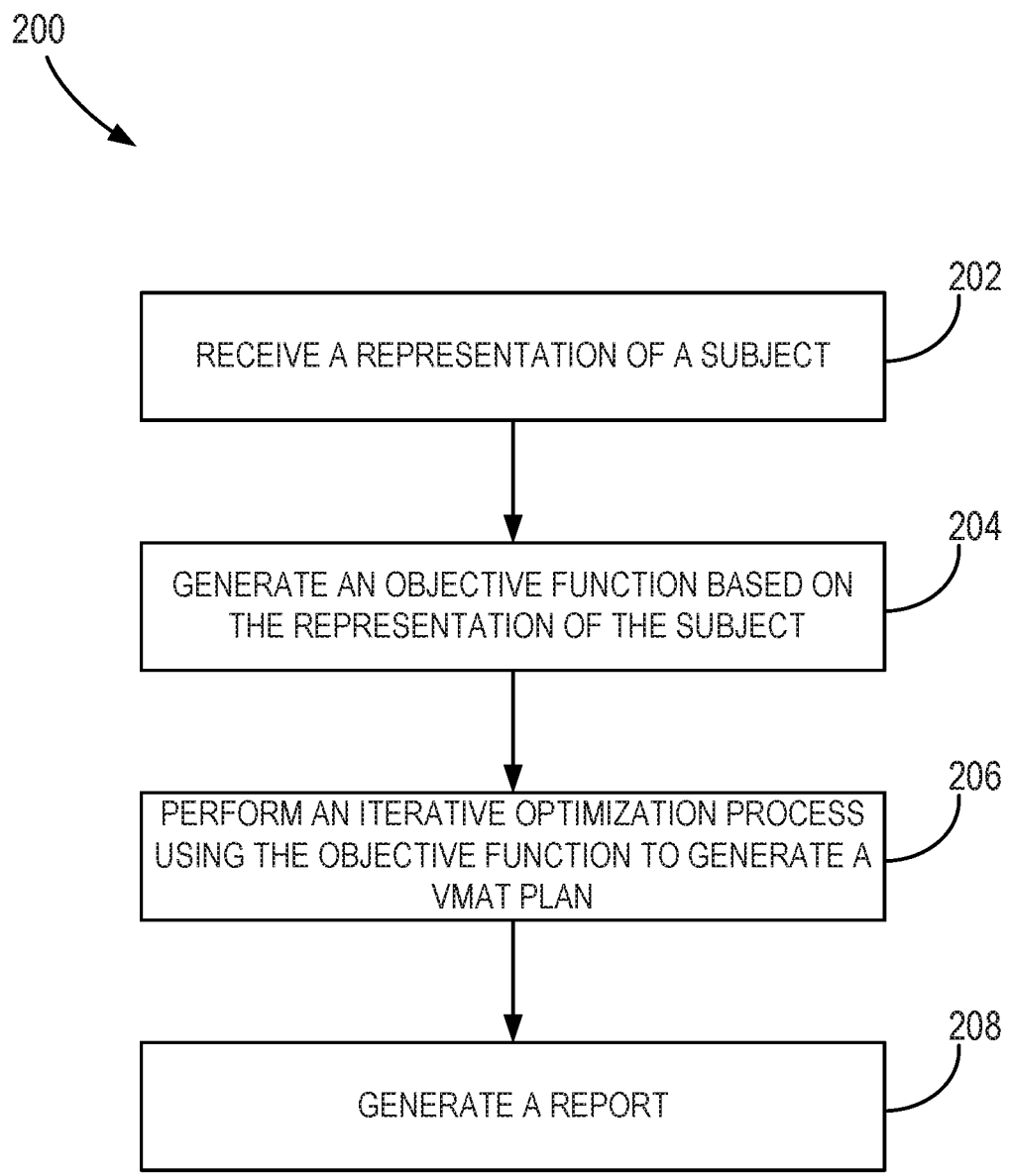
FIG. 2 is a flowchart setting forth steps of a process, in accordance with aspects of the present disclosure.

Referring particularly to FIG. 2, steps of a process 200 in accordance with aspects of the present disclosure are shown. The process 200, or various steps therein, may be carried out using any suitable device, apparatus or system, such as planning workstation, or using, or in cooperation with, a system as described with reference to FIG. 3.

In some implementations, steps of the process 200 may be performed using at least one processor configured to execute programming or instructions stored in non-transitory computer readable media. The processor may be a general-purpose processor. Alternatively, the processor may be a dedicated or application-specific processor having non-transitory programming or executable instructions hardwired therein. In one non-limiting example, steps of the process 200 may be carried out using an optimizer engine or a dedicated processing module of a computer.

The process 200 may begin at process block 202 with receiving a representation of a subject. In some aspects, the representation may include images acquired from the subject, such images obtained during a diagnostic or a treatment simulation protocol. The images may be acquired using various imaging modalities, including computed tomography ("CT"), magnetic resonance ("MR"), positron emission tomography ("PET"), and other imaging modalities, which may include temporal information as well. In addition, the representation may also include information related to target and non-target volumes of interest ("VOI"). This may include contours of target (e.g. diseased tissues) and non-target (e.g. normal tissues) structures, obtained using various manual, automated and semi-automated segmentation techniques. In addition, dosing requirements according to clinician prescription may also be received at process block 202 in the representation of the subject.

Then, an optimization framework may implemented at process block 204, as described below. In the framework, an objective function incorporating dynamic collimator rotation may be generated using the representation received. Specifically, collimator terms, as well as a dose fidelity term and fluence terms may be included in the optimization function, allowing optimization of collimator rotation in addition to other beam characteristics.

VMAT plans may be generated by performing an iterative optimization process using the objective function, as indicated by process block 206. To solve the optimization function during the iterative optimization process, a block approach may be adopted. For example, a Primal Dual Hybrid Gradient ("PDHG") algorithm may be used.

A report may then be generated using the generated plan, as indicated by process block 208. The report may be in any form and include a variety of information, including information describing beam characteristics and delivery configurations optimized using an optimization framework, in accordance with the present disclosure. For example, the report may include a representation reflecting aperture shapes at selected beam or gantry angles, as well as collimator rotations corresponding to the apertures. The report may be provided as output to a display.

In some aspects, report may include information or instructions suitable for execution by a therapy system, such as the VMAT system described with reference to FIG. 3. For instance, the report may include control signals directing the therapy system to select optimized beam angles in relation to the subject, as well as apertures and collimator rotations corresponding to the selected beam angles. The control signals may also direct the therapy system to irradiate the subject for specified periods of time using the optimized apertures and collimator rotations.

The present optimization framework will now be described. In this framework, referred to as dynamic collimator volumetric modulated arc therapy ("DC_VMAT") optimization, an objective function can be generated using the following form:

$$\operatorname*{argmin}_{f,c,u} \frac{1}{2} \left\| W \left( \sum_{b=1}^{n_b} \sum_{a=1}^{n_a} (A_{ba} f_{ba}) - d \right) \right\|_2^2 + \qquad \text{Eqn. (1)}$$

$$\sum_{b=1}^{n_b} \sum_{a=1}^{n_a} \left( \lambda_1 \| D_{1_{ba}} f_{ba} \|_1 + \lambda_2 \| D_{2_{ba}} f_{ba} \|_1 \right) +$$

$$\text{Node cost } (b, \alpha) = \left\| W \left( \sum_{b=1}^{n_b} \sum_{a=1}^{n_a} (A_{ba} c_{ba}) - d \right) \right\|_2^2 \qquad \text{Eqn. (2)}$$

$$\text{Edge cost } ((b_1, \alpha_1), (b_2, \alpha_2)) = \begin{cases} \max(0, \|\alpha_1 - \alpha_2\|^2 - \eta) + k \|u(b_2, \alpha_2) - u(b_1, \alpha_1)\|_x^2 & \text{if } \|b_1 - b_2\| = 1 \\ \infty & \text{if } \|b_1 - b_2\| \neq 1 \end{cases}$$

-continued $$\frac{1}{2} \sum_{b=1}^{n_b} \sum_{a=1}^{n_a} \left( \gamma_1 \left( \left\| \sqrt{diag(u_{ba})} \, (f_{ba} - c_{ba}) \right\|_2^2 + \right. \right.$$

$$\left\| \sqrt{diag(1 - u_{ba})} \, f_{ba} \right\|_2^2 \right) + \gamma_2 (1 - P_{ba}) \| f_{ba} \|_2 ) +$$

$$\sum_{b=1}^{n_b} \sum_{a=1}^{n_a} \left( g_1 \| D_{1_{ba}} u_{ba} \|_1 + g_2 \| D_{2_{ba}} u_{ba} \|_1 \right)$$

subject to $f \geq 0, 0 \leq u \leq 1$ where $f_{ba}$, $c_{ba}$, and $u_{ba}$ are the optimization variables. $f_{ba}$ is the vectorized fluence map, $c_{ba}$ is a value that $f_{ba}$ approaches within an aperture, and $u_{ba}$ is the aperture variable, which approaches 1 where the corresponding beamlet is on, and approaches 0 elsewhere. Beam angles are indexed by b, collimator rotation or collimator angles are indexed by α, and x and y are indices for a beamlet at a given beam angle b and collimator angle α. The fluence to dose transformation matrix is denoted by $A_{ba}$, and the desired dose, d, may be set to a prescription dose at the planning target volume ("PTV"), for example, and zero elsewhere. Weightings of these structures or terms can be controlled by a diagonal matrix W. The derivative matrices, $D_{1_{ba}}$ and $D_{2_{ba}}$, take the horizontal and vertical derivative of the fluence and aperture, respectively.

The first term in the objective function of Eqn. 1, referred to herein as the dose fidelity or dose penalty term, minimizes a dose distribution by penalizing deviation from the prescription dose. In some aspects, the dose fidelity term may be an L2-norm term. The second term, or first fluence term, encourages or directs the optimization process to ensure smooth fluence mapping between successive apertures. As referred to herein, smoothness in fluence mapping refers to a continuous or semi-continuous change in fluence between apertures. The third term, or second fluence term, encourages fluence mapping with an average fluence intensity. The fourth term, or first collimator term, calculates the cost of collimator rotation. The fifth term, or second collimator term, encourages or directs the optimization process to ensure smooth collimator rotation between successive beam or gantry angles. As referred to herein, smoothness in collimator rotation refers to a continuous or semi-continuous change in rotation angle between beams. In some implementations, smoothness in fluence mapping or collimator rotation may depend on or take into consideration machine constraints, such as temporal and/or spatial restrictions on movement (e.g. collimator rotation resolution, speed and limits) or restrictions on radiation delivery.

$P_{ba}$ in the objective function of Eqn. 1 is a parameter controlling collimator angle for each selected beam, decided from a Dijkstra's graph as follows:

To create an optimized DC_VMAT plan, pencil beams of all selected beams and all selected collimator rotations may be pre-calculated. The optimization problem of Eqn. 1 may then be solved using a PDHG algorithm, for example. In this approach, the optimization may be broken down into simpler blocks or sub-steps.

Figure 3:
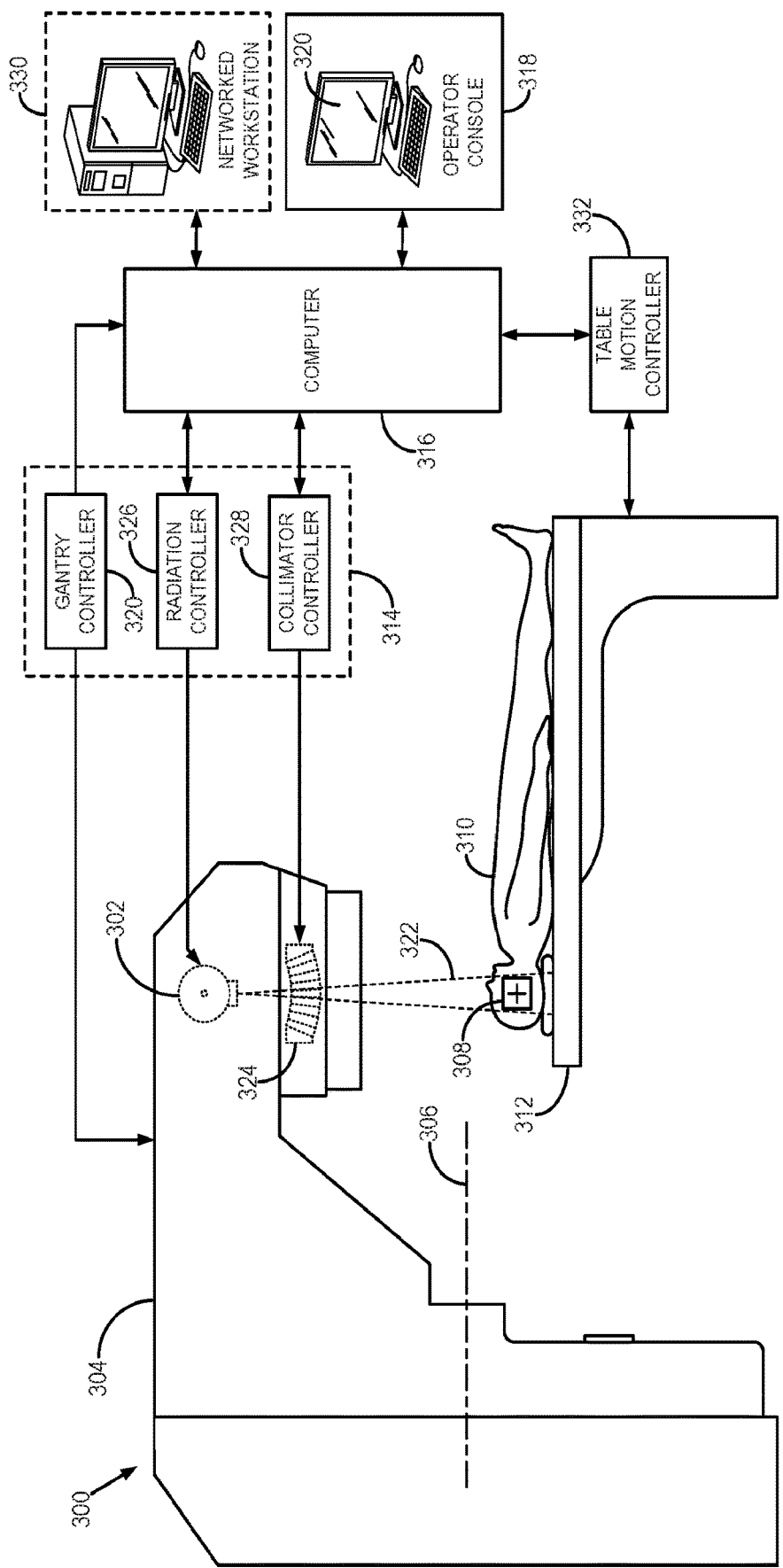
FIG. 3 is a block diagram of an example volumetric modulated arc therapy ("VMAT") system, in accordance with aspects of the present disclosure.

Referring now to FIG. 3, an example of a volumetric modulated arc therapy ("VMAT") system 300 that may be used when practicing the present invention. The VMAT system 300 includes a radiation source 302, such as an x-ray source, that is housed at an end of a rotatable gantry 304 that rotates about a rotation axis 306. The rotatable gantry 304 allows the radiation source 302 to be aligned in a desired manner with respect to a target volume 308 in a subject 310 positioned on a subject table 312. A control mechanism 314 controls the rotation of the gantry 304 and the delivery of radiation from the radiation source 302 to the target volume 308.

The VMAT system 300 includes a computer 316 that receives commands and scanning parameters from an operator via a console 318, or from a memory or other suitable storage medium. An associated display 320 allows the operator to observe data from the computer 316, including images of the subject 310 that may be used to review or modify the treatment plan, and to position the subject 310 by way of appropriately adjusting the position of the subject table 312. The operator supplied commands and parameters may also be used by the computer 316 to provide control signals and information to the control mechanism 314.

The radiation source 302 produces a radiation beam 322, or "field," that is modulated by a collimator 324. The collimator 324 may include an MLC that is composed of a plurality of independently adjustable collimator leaves. In such a configuration, each leaf in the collimator 324 is composed of an appropriate material that inhibits the transmission of radiation, such as a dense radiopaque material, and may include lead, tungsten, cerium, tantalum, or related alloys.

The radiation source 302 is mounted on a rotatable gantry 304 that rotates about a rotation axis 306 so that the radiation beam 322 may irradiate the target volume 308 in the subject 310 from a variety of gantry angles, $\theta_i$. The radiation source 302 is controlled by a radiation controller 326 that forms a part of the control mechanism 314, and which provides power and timing signals to the radiation source 302.

A collimator controller 328, which forms a part of the control mechanism 314, controls the movement of each of the collimator leaves in and out of its corresponding sleeve. The collimator controller 328 moves the collimator leaves rapidly between their open and closed states to adjust the aperture shape of the collimator 324 and, therefore, the shape and fluence of the radiation beam 322. In addition, the collimator controller 328 also controls the rotation angle of the collimator 328. The collimator controller 328 receives instructions from the computer 316 to allow program control of the collimator 324.

A gantry controller 330, which forms a part of the control mechanism 314, provides the signals necessary to rotate the gantry 304 and, hence, to change the position of the radiation source 302 and the gantry angle, $\theta_i$, of the radiation beam 322 for the radiation therapy. The gantry controller 330 connects with the computer 316 so that the gantry 304 may be rotated under computer control, and also to provide the computer 316 with a signals indicating the gantry angle, $\theta_i$, to assist in that control. The position of the subject table 312 may also be adjusted to change the position of the target volume 308 with respect to the radiation source 302 by way of a table motion controller 332, which is in communication with the computer 316.

During operation of the VMAT system 300, the collimator controller 328 receives, from the computer 316, segmentation information indicating the aperture shape to be used for each beam or gantry angle, $\theta_i$, during each sweep of the radiation source 302. The segmentations describe the intensity of the radiation beam 322 that is desired for each gantry angle, $\theta_i$. In addition, the collimator controller 328 also receives rotation information to control the rotation angle of the collimator 328.

In some aspects, the computer 316 may be configured to utilize an optimization framework, as described, to generate a DC_VMAT plan using programming or instructions stored in non-transitory computer readable media. To this end, the computer 316 may include an optimizer engine or a dedicated processing module configured specifically to carry out steps for generating VMAT plans. Alternatively, treatment planning may be performed using an external or networked workstation 330, such as a treatment planning workstation, in communication with the computer 316.

Among other steps, the computer 316 may be configured to receive a representation of a subject using an input, and generate an objective function based on the representation of the subject. As described, the representation may include various images, or image data, acquired from a subject, for instance, during a treatment simulation protocol. To this end, the computer 316 may be configured to control an imager (not shown in FIG. 3) to acquire the imaging data. In addition, as described, the representation received the computer 316 may also include other information, such contours of diseased and normal tissue structures, dosing requirements or dose constraints based upon predetermined dose prescriptions, and so forth.

The computer 316 may then generate an objective function based on the representation of the subject, and generate a VMAT plan by performing an iterative optimization process using the objective function. In some implementations, the VMAT plan generated by the computer 316 may be configured in accordance with the mechanical and operational specifications of the system 300. To this end, the computer 316 may have such information stored in a memory, or may acquire such information from the control mechanism 314 or other system, or may determine such information.

The computer 316 may then report results associated with the VMAT plan generated to a user via the display 320. In addition, the computer 316 may also generate and provide control signals and information to the control mechanism 314 to execute the VMAT plan and treat the subject.

Figure 4:
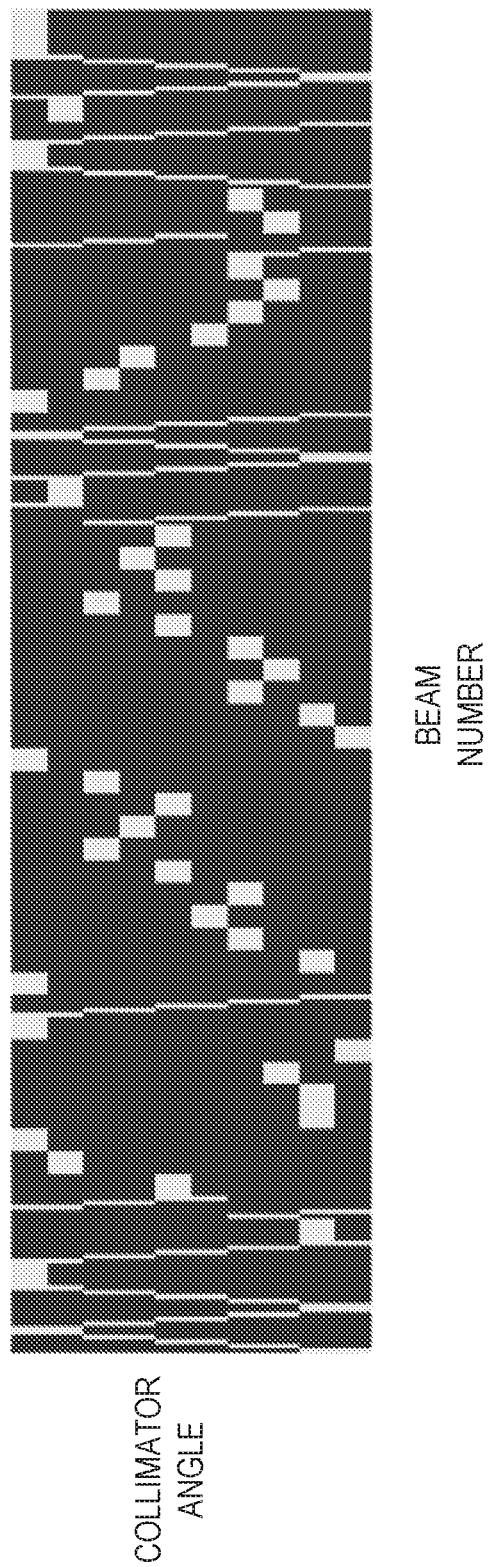
FIG. 4 is an example collimator angle map where each row represents one collimator angle and each column represents one beam.

To demonstrate the advantage of the present approach over prior static methods, a case study was performed on a subject diagnosed with gliobastoma multiforme ("GBM") subject. In particular, a VMAT plan was generated using static collimator volumetric modulated arc therapy ("SC_VMAT") technique, and compared to a DC_VMAT plan generated in accordance with the present disclosure. As an example, FIG. 4 shows a collimator angle map corresponding to the DC_VMAT plan. The figure illustrates dynamic collimator rotation, with each row representing one collimator angle and each column representing one beam.

Figure 5:
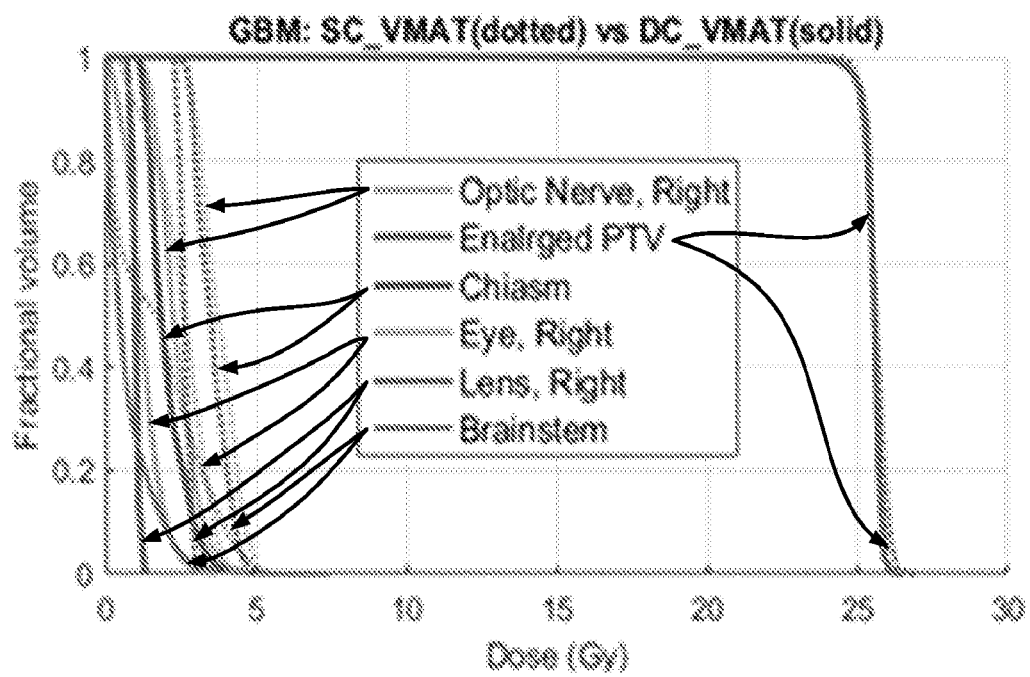
FIG. 5 is a graph comparing dose volume histograms obtained using a static collimator volumetric modulated arc therapy ("SC_VMAT") method (dotted) and a dynamic collimator volumetric modulated arc therapy ("DC_VMAT") method (solid), in accordance with aspects of the present disclosure.
Figure 6:
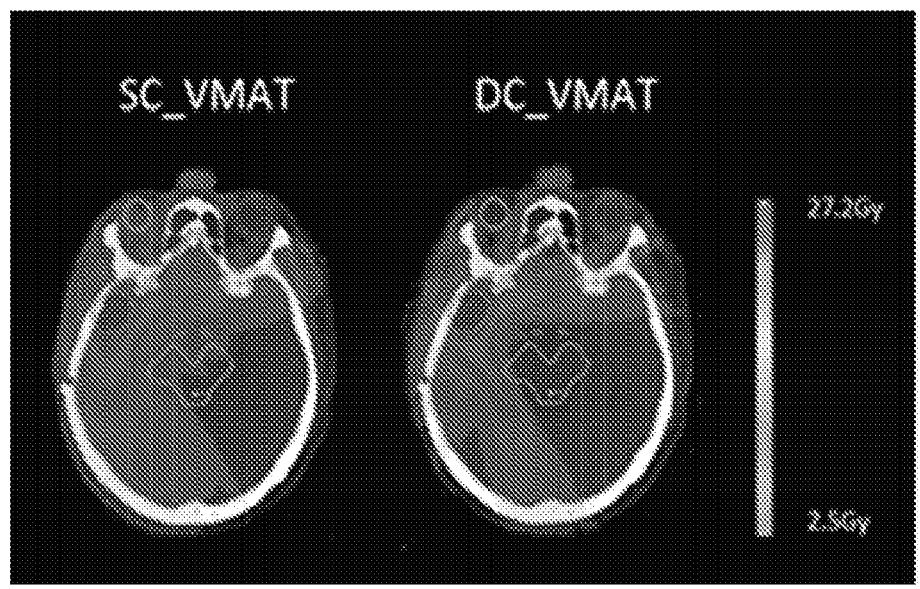
FIG. 6 is an image comparing dose distributions obtained using a SC_VMAT method and a DC_VMAT method, in accordance with aspects of the present disclosure.

Dose distributions and dose volume histograms ("DVH") were then computed based on the SC_VMAT and DC_VMAT plans. FIGS. 5 and 6 show examples comparing DVHs and dose distributions of different structures. As appreciated from the figures, doses to critical structures were reduced by about 4% to 6% of the prescription dose using the present DC_VMAT approach. Furthermore, the number of arcs required to deliver treatment was reduced from 2 to 1 when using the present approach. These results demonstrate not only the novelty and advantages of the present approach, but also its feasibility and practicality in the clinic.

Figure 7:
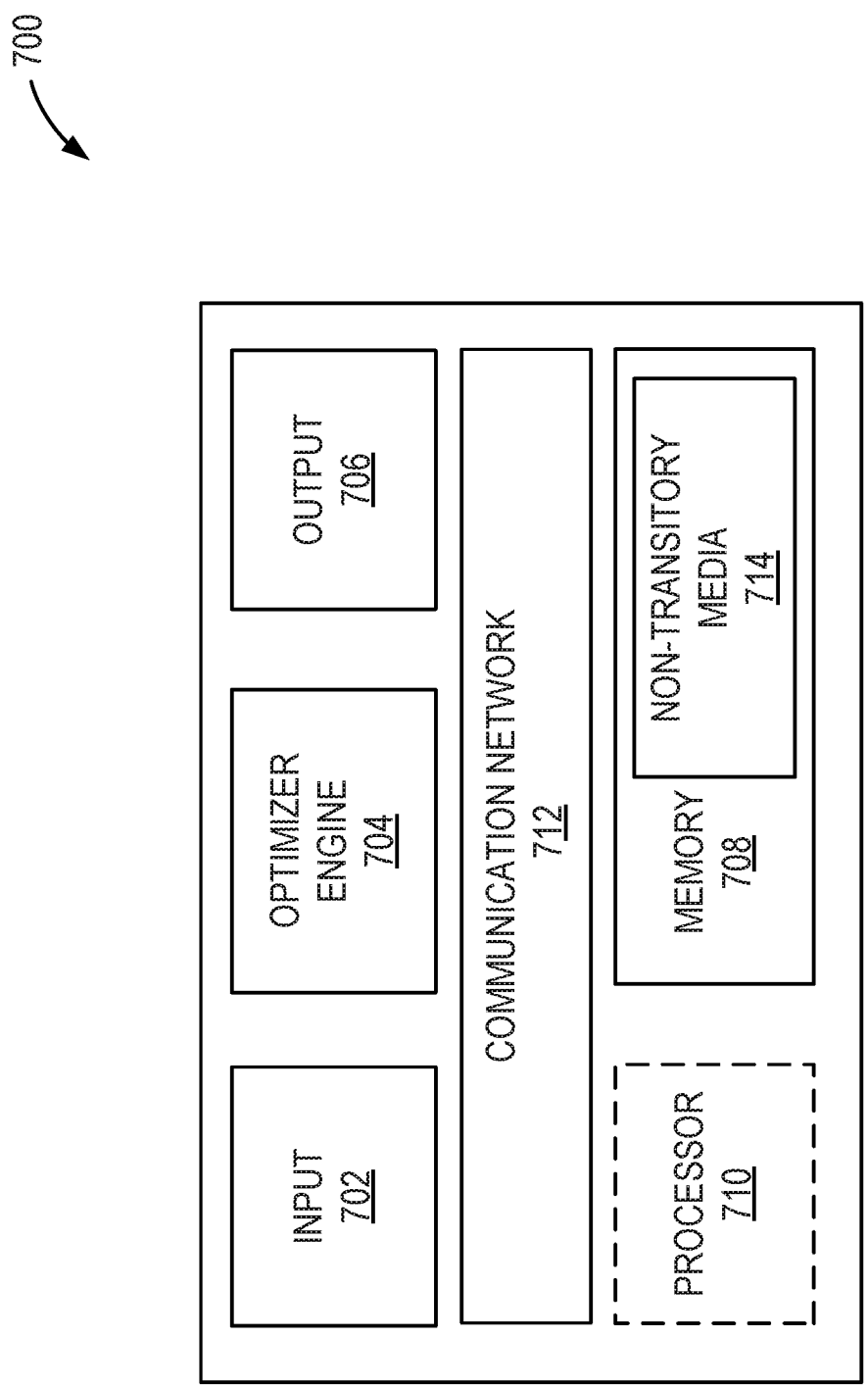
FIG. 7 is a block diagram of an example system, in accordance with aspects of the present disclosure.

Referring now to FIG. 7, a system 700 in accordance with aspects of the present disclosure is shown. In some applications, the system 700 may be a treatment planning system. In general, the system 700 includes an input 702, an optimizer engine 704, an output 706, a memory 708, and optionally a separate processor 710. The system 700 also includes a communication network 712 configured to facilitate the transfer of data, signals and other information between the various elements of the system 700.

The input 702 is configured to receive input and feedback from a user and may include various elements such as a mouse, a keyboard, buttons, switches, toggles, knobs, touch screens, or other touch-responsive elements, as well as ports, connectors, and receptacles for flash-memory, USB sticks, cables, and so on.

The optimizer engine 704 may include various components hardware for carrying out methods in accordance with the present disclosure. For example, the optimizer engine 704 may include a central processing unit ("CPU") with one or more cores, and optionally a graphical processing unit ("GPU"). In some implementations, the optimizer engine 704 is programmed, or includes executable instructions hardwired therein, to carry out an optimization framework to generate and provide reports corresponding to generated VMAT plans, as described.

The output 706 may be configured to provide a report by way of various output elements, including screens, displays, LEDs, LCDs, speakers and so on.

The memory 708 may include various memory elements where a number of types of data (e.g., internal data, external data instructions, software codes, status data, diagnostic data, etc.) may be stored. As an example, the memory 712 may include random access memory ("RAM"), dynamic random access memory ("DRAM"), electrically erasable programmable read-only memory ("EEPROM"), flash memory, and the like. In some implementations, the memory 708 may also include non-transitory computer-readable media 714, which may include instructions for operating the system 700 and carrying out steps of methods in accordance with present disclosure. The memory 708 may store various information including subject information, prescription information, treatment plan information, and so forth.

The communication network 712 may include a variety of communication capabilities and circuitry, including various wiring, components and hardware for electronic, radiofrequency ("RF"), optical and other communication methods. By way of example, the communication network 712 may include parallel buses, serial buses, and combinations thereof. Example serial buses may include serial peripheral interface (SPI), I2C, DC-BUS, UNI/O, 1-Wire, and others. Example parallel buses may include ISA, ATA, SCSI, PIC, IEEE and others.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for treating a subject using a dynamic collimator volumetric modulated arc therapy ("VMAT") plan, the method comprising:
   receiving a representation of the subject comprising information related to target and non-target volumes of interest;
   generating an objective function based on the representation of the subject, wherein the objective function accounts for dynamic collimator rotation;
   performing an iterative optimization process using the objective function to generate the dynamic collimator VMAT plan;
   identifying an aperture shape for a plurality of apertures by minimizing the objective function in the iterative optimization process; and
   irradiating the subject in accordance with the dynamic collimator VMAT plan.

2. The method of claim 1, wherein the representation comprises at least one image of the subject acquired using at least one of computed tomography ("CT"), magnetic resonance imaging ("MRI"), or positron emission tomography ("PET").

3. The method of claim 1, wherein the objective function comprises a first collimator term and a second collimator term.

4. The method of claim 3, wherein the first collimator term calculates a cost of collimator rotation.

5. The method of claim 3, wherein the second collimator term directs smooth collimator rotation between gantry angles.

6. The method of claim 3, wherein the objective function further comprises a dose fidelity term that penalizes deviation from a prescription dose.

7. The method of claim 6, wherein the dose fidelity term is an L2-norm term.

8. The method of claim 3, wherein the objective function further comprises a first fluence term and a second fluence term, wherein the first fluence term directs smooth fluence mapping between successive apertures of the plurality of apertures and the second fluence term directs fluence mapping with an average fluence intensity.

9. The method of claim 1, wherein the method further comprises minimizing the objective function in the iterative optimization process to identify the plurality of apertures, each defined by a fluence, the aperture shape and a collimator rotation.

10. The method of claim 9, wherein the method further comprises applying a Primal Dual Hybrid Gradient ("PDHG") algorithm to minimize the objective function.

11. The method of claim 1, wherein the method further comprises delivering the dynamic collimator VMAT plan using a VMAT system.

12. The method of claim 1, wherein the dynamic collimator rotation includes a rotation of a collimator about a first axis that is different than an axis of rotation of a rotatable gantry that includes a radiation source.

13. A volumetric modulated arc therapy ("VMAT") system comprising:
   a radiation source configured to generate and direct radiation to a subject;
   a gantry housing the radiation source and configured to rotate about an axis of rotation;
   a control mechanism configured to control the rotation of the gantry and a delivery of radiation from the radiation source to a target volume in the subject; and
   a computer in communication with the control mechanism, wherein the computer is configured to:
      receive a representation of the subject comprising information related to target and non-target volumes of interest;
      generate an objective function based on the representation of the subject, wherein the objective function accounts for dynamic collimator rotation;
      perform an iterative optimization process using the objective function to generate a dynamic collimator VMAT plan;
      identify an aperture shape for a plurality of apertures by minimizing the objective function in the iterative optimization process; and
      generate and provide control signals to the control mechanism, in accordance with the dynamic collimator VMAT plan, to irradiate the subject.

14. The system of claim 13, wherein the objective function comprises a first collimator term and a second collimator term.

15. The system of claim 14, wherein the first collimator term calculates a cost of collimator rotation.

16. The system of claim 14, wherein the second collimator term directs smooth collimator rotation between gantry angles.

17. The system of claim 14, wherein the objective function further comprises a dose fidelity term that penalizes deviation from a prescription dose.

18. The system of claim 17, wherein the dose fidelity term is an L2-norm term.

19. The system of claim 14, wherein the objective function further comprises a first fluence term and a second fluence term, wherein the first fluence term directs smooth fluence mapping between successive apertures of the plurality of apertures and the second fluence term directs fluence mapping with an average fluence intensity.

20. The system of claim of claim 13, wherein the dynamic collimator rotation includes a rotation of a collimator about a first axis that is different than the axis of rotation of the gantry housing.

* * * * *